(12) United States Patent
Bailey et al.

(10) Patent No.: US 11,596,767 B2
(45) Date of Patent: Mar. 7, 2023

(54) DEPLOYABLE TUBE APPARATUS FOR DELIVERY OF AN ELONGATE DEVICE AND METHODS OF USE

(71) Applicant: INTUITIVE SURGICAL OPERATIONS, INC., Sunnyvale, CA (US)

(72) Inventors: David W. Bailey, Portola Valley, CA (US); Maxwell J. Bean, Orem, UT (US); Larry L. Howell, Orem, UT (US); Brian D. Jensen, Orem, UT (US); Hannah Rose Lutz, Provo, UT (US); Spencer P. Magleby, Provo, UT (US); Brandon Scott Sargent, Provo, UT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1094 days.

(21) Appl. No.: 16/243,535

(22) Filed: Jan. 9, 2019

(65) Prior Publication Data

US 2019/0216447 A1 Jul. 18, 2019

Related U.S. Application Data

(60) Provisional application No. 62/639,160, filed on Mar. 6, 2018, provisional application No. 62/616,810, filed on Jan. 12, 2018.

(51) Int. Cl.
*A61M 25/00* (2006.01)
*A61B 17/34* (2006.01)
(Continued)

(52) U.S. Cl.
CPC ..... *A61M 25/0054* (2013.01); *A61B 17/3417* (2013.01); *A61B 17/3421* (2013.01);
(Continued)

(58) Field of Classification Search
CPC ............... B31F 1/0003; A61B 17/3417; A61B 17/3421; A61B 1/3132;
(Continued)

(56) References Cited

U.S. PATENT DOCUMENTS 3,177,987 A * 4/1965 Swaim ................... H01Q 1/087
138/156
3,361,377 A 1/1968 Trexler, Jr.
(Continued)

OTHER PUBLICATIONS

BRBF System, "BRBF Introduction, Concept of Buckling Restrained Brace, Pinned Brace, Powercat, Welded Brace, Wildcat," retrieved on Sep. 19, 2018, Retrieved from the internet URL: http://www.starseismic.eu/BRBF_system, 6 pages.
(Continued)

*Primary Examiner* — Richard G Louis
(74) *Attorney, Agent, or Firm* — Haynes and Boone, LLP

(57) ABSTRACT

A deployable tube apparatus may include a spool and a flexible sheet coiled about the spool in a laterally unfurled condition. The flexible sheet may have a first lateral margin and a second lateral margin, and may be deployable from the laterally unfurled condition with the first and the second lateral margins spaced from each other to a deployed tubular condition where the first and the second lateral margins are coupled to each other to form an enclosed lumen. The deployable tube apparatus may provide lateral support to an elongated flexible instrument, such as a catheter. Methods of creating and using the deployable tube apparatus are described.

20 Claims, 13 Drawing Sheets

(51) Int. Cl.
*A61B 34/00* (2016.01)
*A61B 1/313* (2006.01)
*A61M 25/01* (2006.01)
*A61B 17/00* (2006.01)
*A61B 34/20* (2016.01)
*A61B 34/30* (2016.01)

(52) U.S. Cl.
CPC ............. *A61B 34/70* (2016.02); *A61M 25/00* (2013.01); *A61B 1/3132* (2013.01); *A61B 2017/00318* (2013.01); *A61B 2017/00336* (2013.01); *A61B 2017/00982* (2013.01); *A61B 2034/2061* (2016.02); *A61B 2034/301* (2016.02); *A61M 25/0113* (2013.01); *A61M 2025/0034* (2013.01)

(58) Field of Classification Search
CPC ........... A61B 2017/00318; A61B 2017/00336; A61B 2017/00982; A61B 2034/2061; A61B 2034/301; A61B 34/30; A61B 2034/2051; A61M 25/00; A61M 25/0054; A61M 25/0113; F02F 2200/00
See application file for complete search history.

(56) References Cited

U.S. PATENT DOCUMENTS

2012/0041537 A1* 2/2012 Parker ................. A61F 2/95
623/1.11
2017/0265953 A1* 9/2017 Fenech ................. A61B 90/50

OTHER PUBLICATIONS

Butler J., et al., "Highly Compressible Origami Bellows for Harsh Environments," Proceedings of the ASME 2016 International Design Engineering Technical Conferences and Computers and Information in Engineering Conference (IDETC/CIE), DETC2016-59060, Aug. 2016, 11 pages.
Butler J., et al., "Highly Compressible Origami Bellows for Microgravity Drilling-Debris Containment," AIAA Space and Astronautics Forum and Exposition, 2017, 16 pages.
Dearden J., et al., "Cylindrical Cross-axis Flexural Pivots Precision Engineering," Jan. 2018, vol. 51, pp. 604-613.
Dearden J., et al., "Inverted L-Arm Gripper Compliant Mechanism," Journal of Medical Devices, Mar. 2017, vol. 11 (3), pp. 034502-1-034502-6.
Dearden J.L., "Design and Analysis of Two Compliant Mechanism Designs for Use in Minimally Invasive Surgical Instruments," M.S. thesis, Brigham Young University, Jul. 2016, 85 pages.
Grames C.L., "Design and Manufacture of Mesoscale Robot-Actuated Surgical instruments," M.S. thesis, Brigham Young University, Nov. 2015, 67 pages.
Grames C.L., et al., "A Compact 2 Degree of Freedom Wrist for Robot-Actuated Surgery and Other Applications," Proceedings of the ASME 2016 International Design Engineering Technical Conferences and Computers and Information in Engineering Conference, Aug. 2016, 12 pages.
Grames C.L., et al., "A Meso-Scale Rolling-Contact Gripping Mechanism for Robotic Surgery," Proceedings of the ASME 2015 International Design Engineering Technical Conferences &Computers and Information in Engineering Conference, Aug. 2015, 11 pages.
Jensen B.D., et al., "Design and Fabrication of Millimeter-Scale Crossed-Cylinder Wrist Mechanism with Two Degrees of Freedom," Microactuators and Micromechanisms, 2015, pp. 133-141.
Jianguo C., et al., "Bistable Behavior of the Cylindrical Origami Structure With Kresling Pattern," Journal of Mechanical Design, Jun. 2015, vol. 137 (6), pp. 061406-1-061406-8.
Kresling B., Natural Twist Buckling in Shells: from the Hawkmoth's Bellow to the Deployable "Kresling-pattern" and Cylindrical "Miura-ori", Proceedings of the 6th International Conference on Computation of Shell and Spatial Structures, IASS-IACM 2008:"Spanning Nano to Mega", May 2008, 4 pages.
Pellegrino S., "Large Retractable Appendages in Spacecraft," Journal of Spacecraft and Rockets, Nov.-Dec. 1995, vol. 32 (6), pp. 1006-1014.
Tanner J.D., "Design and Analysis of Robotically-Controlled Minimally invasive Surgical Instruments," M.S. thesis, Brigham Young University, Nov. 2014, 91 pages.
Tanner J.D., et al., "Millimeter-Scale Robotic Mechanisms Using Carbon Nanotube Composite Structures," Journal of Mechanisms and Robotics, May 2015, vol. 7 (2), pp. 021001-1-021001-7.
Thomson M.W., "Deployable and Retractable Telescoping Tubular Structure Development," Astro Aerospace Corporation, California, 1994, pp. 323-338.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

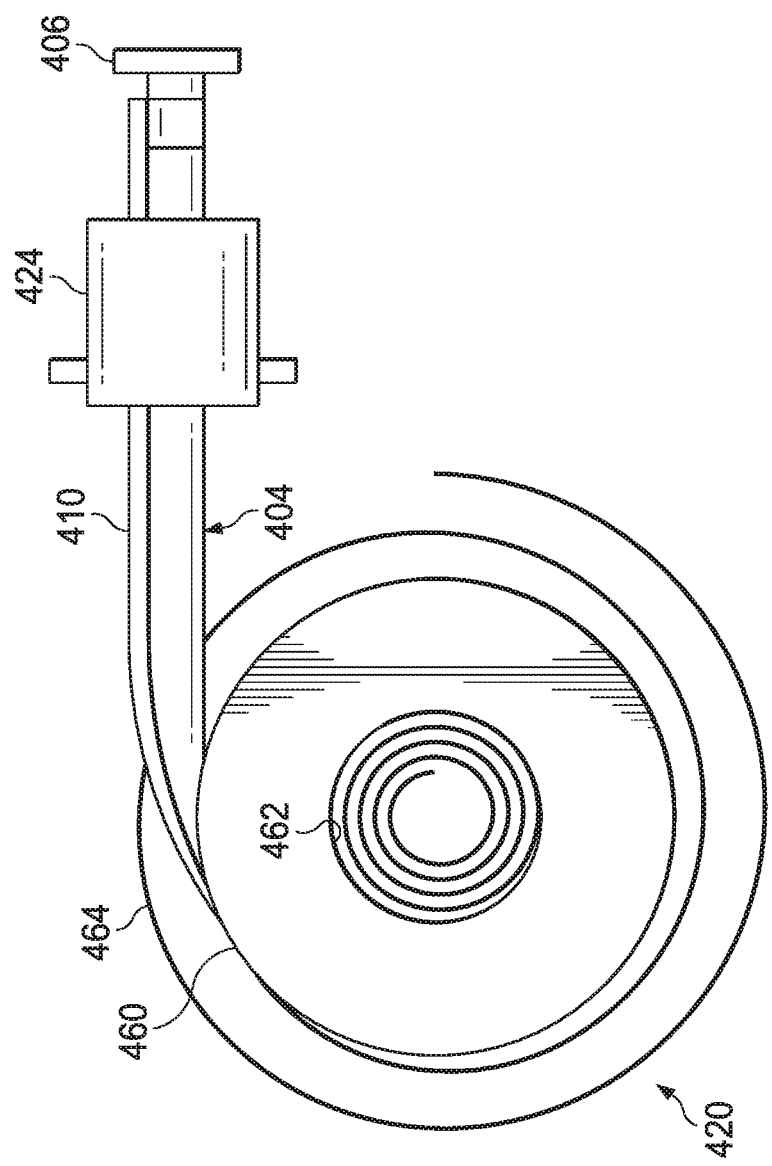

DEPLOYABLE TUBE APPARATUS FOR DELIVERY OF AN ELONGATE DEVICE AND METHODS OF USE

CROSS-REFERENCE TO RELATED APPLICATIONS

This application claims the benefit of U.S. Provisional Application 62/616,810 filed Jan. 12, 2018, and U.S. Provisional Application 62/639,160 filed Mar. 6, 2018 all of which are incorporated by reference herein in their entirety.

FIELD

The present disclosure is directed to systems and methods for navigating a patient anatomy to conduct a minimally invasive procedure, and more particularly to apparatus and methods for guiding and supporting the delivery of an elongate device (such as a flexible interventional instrument and/or a steerable interventional instrument) into a patient anatomy.

BACKGROUND

Minimally invasive medical techniques are intended to reduce the amount of tissue that is damaged during interventional procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. Operators may insert minimally invasive medical instruments (including surgical, diagnostic, therapeutic, or biopsy instruments) through these natural orifices or incisions to reach a target tissue location. One such minimally invasive technique is to use a flexible and/or steerable elongate device, such as a flexible catheter, that can be inserted into anatomic passageways and navigated toward a region of interest within the patient anatomy. To reach the target tissue location, a minimally invasive interventional instrument may navigate natural or surgically created passageways in anatomical systems such as the lungs, the colon, the intestines, the kidneys, the heart, the circulatory system, or the like. Control of such an elongate device by medical personnel involves the management of several degrees of freedom including at least the management of insertion and retraction of the elongate device as well as steering of the device. In addition, different modes of operation may also be supported.

Several interventional instruments are made of flexible material that allows for maneuverability through a patient's body. In existing systems, at least a portion of the interventional instrument extending between the patient and a manipulator is unsupported, and the flexible nature of the instrument can cause it to bend, twist, or buckle in an undesirable manner at a point external to the patient's body when force is exerted to insert the instrument into the patient's anatomy. Deformation of the instrument may damage internal components such as optical fiber shape sensors or endoscopic equipment. While current systems may provide adequate support for these types of instruments, additional improvements may be had for guiding and supporting interventional instruments as they are inserted into a patient's anatomy to prevent instrument deformation.

SUMMARY

The implementations of the invention are summarized by the claims that follow the description.

Consistent with some implementations, the present disclosure is directed to a deployable tube apparatus that may include a spool and a flexible sheet coiled about the spool in a laterally unfurled condition. The flexible sheet may have a first lateral margin and a second lateral margin. The flexible sheet may be deployable from the laterally unfurled condition with the first and the second lateral margins spaced from each other to a deployed tubular condition where the first and the second lateral margins are coupled to each other to form an enclosed lumen.

In some aspects, a fastener portion may selectively fasten the first and the second lateral margins. The deployable tube apparatus may include a guide that selectively fastens and unfastens the fastener when said at least one of the first and the second lateral margins displaces past the guide. The guide may be shaped to deform the flexible sheet between the laterally unfurled condition and the deployed tubular condition. In some aspects, the guide may include a splitter that separates the coupled first and the second lateral margins, and a slide fastener having an orifice through which the first and the second lateral margins pass. The orifice may be sized to cooperate with the first and the second lateral margins to compress the first and the second lateral margins together. In some aspects, the first lateral margin may include a first fastener portion and the second lateral margin may include a second fastener portion attachable to the first fastener portion to maintain the flexible sheet in the deployed tubular condition.

In some exemplary aspects, the present disclosure is directed to a deployable tube apparatus that includes a flexible sheet material having longitudinal length, a first lateral margin, and a second lateral margin. The first and the second lateral margins may extend along the longitudinal length, and the sheet material may be bendable between a laterally unfurled condition where the first and the second lateral margins are spaced from each other and a deployed tubular condition where the first and the second lateral margins are adjacent to each other to form a lumen. At least one of the first and second lateral margins may include a fastener portion that selectively attaches the first and the second lateral margins. The deployable tube apparatus may also include a guide configured to fold the flexible sheet material from the laterally unfurled condition to the deployed tubular condition and to fasten the first and the second lateral margins.

In some aspects, the guide may include a splitter that separates the attached first and the second lateral margins and an opening sized to receive the first and the second lateral margins and compress the first and the second lateral margins toward each other. In some aspects, the deployable tube apparatus may include a spool disposed spatially to the guide, the flexible sheet material from the deployed tubular condition to the laterally unfurled condition.

In some exemplary aspects, the present disclosure is directed to a method of operating a deployable tube apparatus. The method may include unrolling a roll of a flexible sheet material in a laterally unfurled condition. The flexible sheet may have a first lateral margin and may have a second lateral margin spaced apart from the first lateral margin. While unrolling the flexible sheet, the method may include folding the flexible sheet to a tubular condition with the first and the second lateral margins being adjacent to each other. Also while unrolling the flexible sheet, the method may include attaching the first and the second lateral margins to each other to maintain the flexible sheet material in the tubular condition.

In some aspects, the method may also include retracting the flexible sheet in the tubular condition, and while retracting, separating the attached first and the second lateral margins and to unfold the flexible sheet into the laterally unfurled condition. The flexible sheet may be rolled in the laterally unfurled condition.

In yet other exemplary aspects the present disclosure is directed to a deployable tube apparatus for guiding an elongated flexible surgical instrument. The apparatus may include a flexible sheet material having a longitudinal length, a first lateral margin, and a second lateral margin. The first and the second lateral margins may extend along the longitudinal length. The sheet material may be deployable from a laterally unfurled condition with the first and the second lateral margins spaced from each other to a deployed tubular condition where the first and the second lateral margins are adjacent to each other to form a lumen arranged to provide lateral support to the elongated flexible surgical instrument. At least one of the first and second lateral margins may include a fastener that selectively attaches the first and the second lateral margins. The deployable tube apparatus may also include a guide structurally arranged to selectively fasten and unfasten the fastener of said at least one of the first and the second lateral margins when the sheet material displaces past the guide. The guide may be shaped to deform the sheet material between the laterally unfurled condition and the deployed tubular condition.

In some aspects, the guide may include a fixture through which the elongated flexible surgical instrument extends. The fixture may be disposed to align the elongated flexible surgical instrument with the lumen formed by the flexible sheet material when in the deployed tubular condition so that an inner wall of the flexible sheet material in the deployed tubular condition provides lateral support to the elongated surgical instrument.

In yet other exemplary aspects, the present disclosure is directed to a method of operating a deployable tube apparatus to provide support to an elongated flexible surgical instrument. The method may include providing a material sheet in a folded configuration to form a lumen, providing the elongated flexible surgical instrument in the lumen, and while axially displacing the elongated flexible surgical instrument, attaching or separating a first lateral margin and a second lateral margin of the folded sheet about the elongated flexible surgical instrument to provide lateral support to the elongated flexible surgical instrument.

In some aspects, the method may include advancing the elongated flexible surgical instrument through a guide aligned with the lumen of the material sheet. The method may include maintaining a continuous biasing force on the material sheet in the folded configuration to provide stiffness and rigidity of the material sufficient to provide lateral support to the elongated flexible surgical instrument. The method may include creating an enclosed tubular structure about the elongated flexible instrument while axially displacing the surgical instrument.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various implementations and/or configurations discussed.

FIG. 8 is a side view of a diagram of a spool and flexible sheet forming a part of the instrument guiding apparatus of FIG. 5 according to some implementations of the present disclosure.

Figure 1:
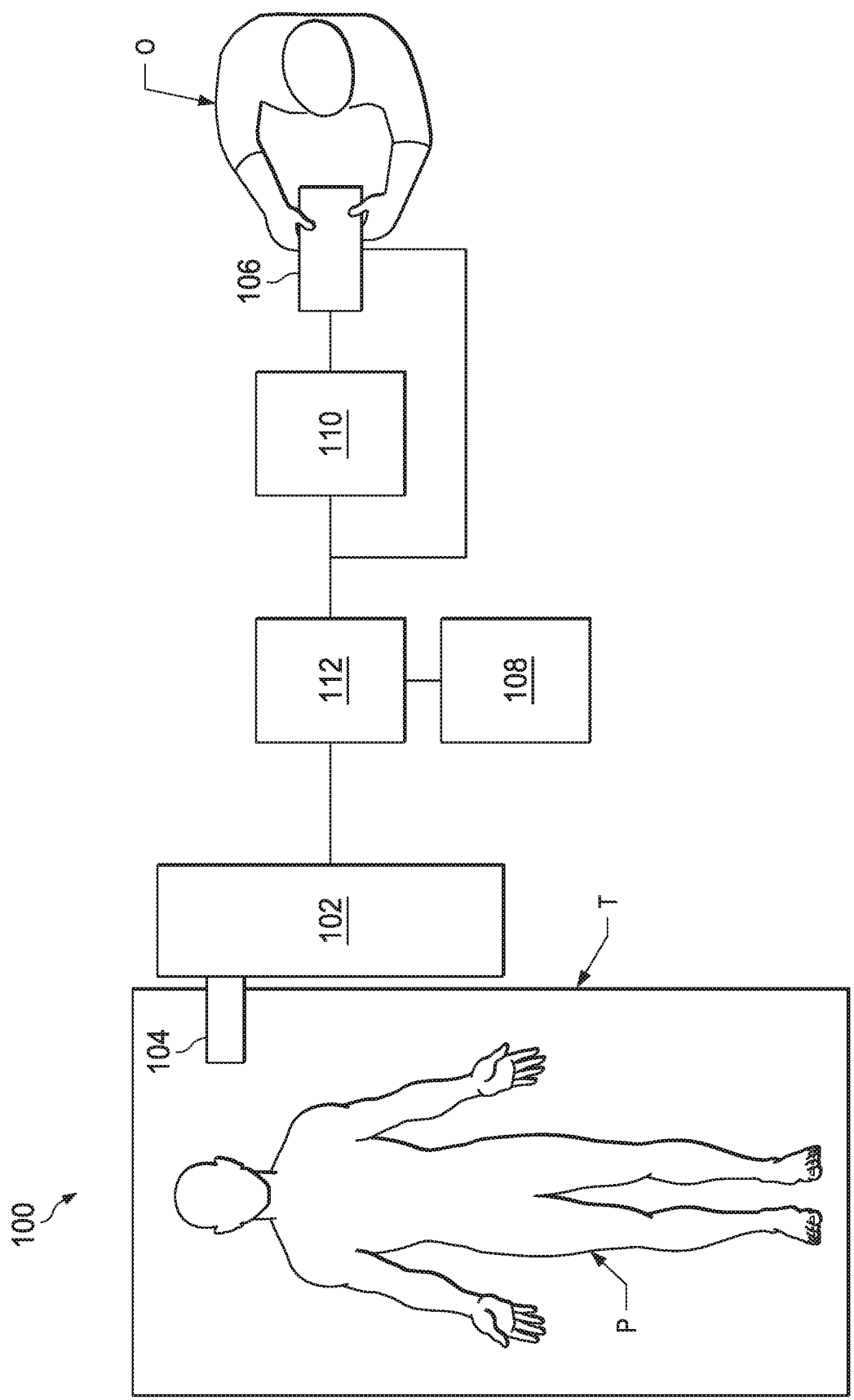
FIG. 1 is a simplified diagram of a teleoperated medical system according to some implementations of the present disclosure.

Implementations of the present disclosure and their advantages are best understood by referring to the detailed description that follows. It should be appreciated that like reference numerals are used to identify like elements illustrated in one or more of the figures, wherein showings therein are for purposes of illustrating implementations of the present disclosure and not for purposes of limiting the same.

DETAILED DESCRIPTION

In the following description, specific details are set forth describing some implementations consistent with the present disclosure. Numerous specific details are set forth in order to provide a thorough understanding of the implementations. It will be apparent, however, to one skilled in the art that some implementations may be practiced without some or all of these specific details. The specific implementations disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one implementation may be incorporated into other implementations unless specifically described otherwise or if the one or more features would make an implementation non-functional.

In some instances well known methods, procedures, components, and circuits have not been described in detail so as not to unnecessarily obscure aspects of the implementations.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some implementations. In some implementations, teleoperated medical system 100 may be suitable for use in, for example, surgical, diagnostic, therapeutic, or biopsy procedures. As shown in FIG. 1, medical system 100 generally includes a manipulator assembly 102 for operating a medical instrument of the medical instrument system 104 in performing various procedures on a patient P. Manipulator assembly 102 is mounted to or near an operating table T. An operator input system 106 (sometimes called a master assembly 106) allows an operator O (e.g., a surgeon, a clinician, or a physician as illustrated in FIG. 1) to view the interventional site and to control manipulator assembly 102 or sub-assemblies within manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102 or sub-assemblies within manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument of the medical instrument system 104. In this manner, the control devices provide operator O with telepresence or the perception that the control devices are integral with medical instruments 104.

In some implementations, the control devices may have more or fewer degrees of freedom than the associated medical instrument of the medical instrument system 104 and still provide operator O with telepresence. In some implementations, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

FIG. 1 is a simplified diagram of a teleoperated medical system 100 according to some implementations. In some implementations, teleoperated medical system 100 may be suitable for use in, for example, surgical, diagnostic, therapeutic, or biopsy procedures. As shown in FIG. 1, the teleoperated system 100 generally includes a manipulator assembly 102 for operating a medical instrument of the medical instrument system 104 in performing various procedures on the patient P. The manipulator assembly 102 is mounted to or near an operating table O. A master assembly 106 allows an operator (e.g., a surgeon, a clinician, or an operator O as illustrated in FIG. 1) to view the interventional site and to control the manipulator assembly 102 or sub-assemblies within manipulator assembly 102.

The master assembly 106 (or master surgeon control inputs assembly 106) may be located at a surgeon's console which is usually located in the same room as operating table O. However, it should be understood that the operator O can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. To provide operator O a strong sense of directly controlling instruments 104 the control devices may be provided with the same degrees of freedom as the associated medical instrument of the medical instrument system 104. In this manner, the control devices provide operator O with telepresence or the perception that the control devices are integral with medical instruments 104.

In some implementations, the control devices may have more or fewer degrees of freedom than the associated medical instruments 104 and still provide the operator O with telepresence. In some implementations, the control devices are manual input devices which move with six degrees of freedom, and which may also include an actuatable handle for actuating instruments (for example, for closing grasping jaws, applying an electrical potential to an electrode, delivering a medicinal treatment, or the like).

The manipulator assembly 102 supports the medical instrument system 104 and may include a kinematic structure of one or more non-servo controlled links (e.g., one or more links that may be manually positioned and locked in place, generally referred to as a set-up structure), a teleoperational structure, and/or a teleoperational manipulator. The manipulator assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the manipulator assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the manipulator assembly. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the clinician or surgeon operator O. The concurrent image may be, for example, a two or three dimensional image captured by an endoscope positioned within the surgical site. In this implementation, the visualization system includes endoscopic components that may be integrally or removably coupled to the medical instrument system 104. However in alternative implementations, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 for displaying an image or representation of the surgical site and medical instrument system(s) 104 generated by sub-systems of the sensor system 108. The display system 110 and the operator input system 106 may be oriented so the operator O can control the medical instrument system 104 and the operator input system 106 with the perception of telepresence.

The display system 110 may also display an image of the surgical site and medical instruments captured by the visualization system. The display system 110 and the control devices may be oriented such that the relative positions of the imaging device in the scope assembly and the medical instruments are similar to the relative positions of the operator's eyes and hands so the operator can manipulate the medical instrument of the medical instrument system 104 and the hand control as if viewing the workspace in substantially true presence. By true presence, it is meant that the presentation of an image is a true perspective image simulating the viewpoint of an operator that is physically manipulating the instrument of the medical instrument system 104.

Alternatively or additionally, the display system 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some implementations, often for purposes of imaged guided surgical procedures, the display system 110 may display a virtual navigational image in which the actual location of the medical instrument of the medical instrument system 104 is registered (i.e., dynamically referenced) with the preoperative or concurrent images/model to present the operator O with a virtual image of the internal surgical site from the viewpoint of the location of the tip of the instrument of the medical instrument system 104. In some examples, the viewpoint may be from a tip of medical instrument of the medical instrument system 104. An image of the tip of the instrument of the medical instrument system 104 or other graphical or alphanumeric indicators may be superimposed on the virtual image to assist the operator O controlling the medical instrument. Alternatively, the instrument of the medical instrument system 104 may not be visible in the virtual image.

In other implementations, the display system 110 may display a virtual navigational image in which the actual location of the medical instrument is registered with preoperative or concurrent images to present the operator O with a virtual image of the medical instrument within the surgical site from an external viewpoint. An image of a portion of the medical instrument or other graphical or alphanumeric indicators may be superimposed on the virtual image to assist the operator O controlling the instrument of the medical instrument system 104. As described herein, visual representations of data points may be rendered to the display system 110. For example, measured data points, moved data points, registered data points, and other data points described herein may be displayed on the display system 110 in a visual representation. The data points may be visually represented in a user interface by a plurality of points or dots on the display or as a rendered model, such as a mesh or wire model created based on the set of data points. In some implementations, a visual representation may be refreshed in the display system 110 after each processing operations has been implemented to alter the data points.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a non-transitory machine-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the manipulator assembly 102, another portion of the processing being performed at the operator input system 106, another portion of the processing being performed at master assembly 106, and the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one implementation, control system 112 supports wireless communication protocols such as Bluetooth, IrDA, HomeRF, IEEE 802.11, DECT, and Wireless Telemetry.

In some implementations, control system 112 may receive force and/or torque feedback from medical instrument of the medical instrument system 104. Responsive to the feedback, control system 112 may transmit signals to master assembly 106. In some examples, control system 112 may transmit signals instructing one or more actuators of manipulator assembly 102 to move medical instrument of the medical instrument system 104. Medical instrument of the medical instrument system 104 may extend into an internal surgical site within the body of patient P via openings in the body of patient P. Any suitable conventional and/or specialized actuators may be used. In some examples, the one or more actuators may be separate from, or integrated with, manipulator assembly 102. In some implementations, the one or more actuators and manipulator assembly 102 are provided as part of a cart positioned adjacent to patient P and operating table T.

The control system 112 may further include a virtual visualization system to provide navigation assistance to operator O when controlling the medical instrument system(s) 104 during an image-guided surgical procedure. Virtual navigation using the virtual visualization system is based upon reference to the acquired preoperative or intra-operative dataset of the anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some implementations, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In some implementations, the teleoperational system may include more than one teleoperational assembly, more than one non-teleoperational assembly (e.g. a robotic assembly or a manual assembly), and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2:
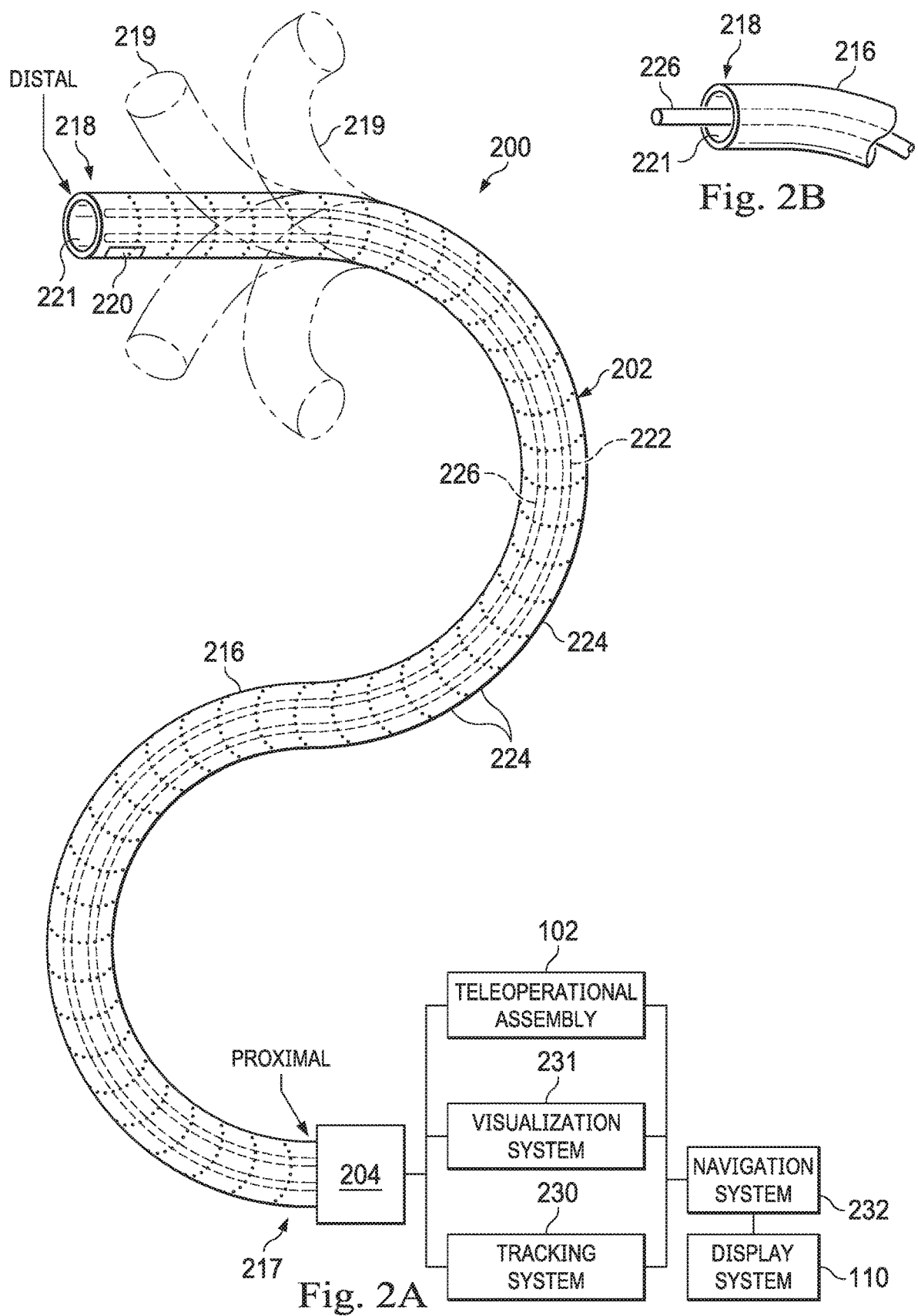
FIG. 2A is a simplified diagram of a medical instrument system according to some implementations of the present disclosure.
FIG. 2B is a simplified diagram of a medical instrument with an extended medical tool according to some implementations of the present disclosure.

FIG. 2A is a simplified diagram of a medical instrument system 200 according to some implementations. In some implementations, medical instrument system 200 may be used as medical instrument of the medical instrument system 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally, medical instrument system 200 may be used to gather (i.e., measure) a set of data points corresponding to locations within anatomic passageways of a patient, such as patient P.

The instrument system 200 includes an elongate device 202 (e.g., a catheter system) coupled to a drive unit 204. The elongate device 202 includes an elongated flexible body 216 having a proximal end 217 and a distal end 218 (or tip portion 218). In one implementation, the flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one implementation, the optical fiber has a diameter of approximately 200 µm. In other implementations, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties. Sensors in some implementations may employ other suitable strain sensing techniques, such as Rayleigh scattering, Raman scattering, Brillouin scattering, and Fluorescence scattering. In some implementations, the shape of the elongate device may be determined using other techniques. For example, a history of the distal end pose of flexible body 216 can be used to reconstruct the shape of flexible body 216 over the interval of time. In some implementations, tracking system 230 may optionally and/or additionally track distal end 218 using a position sensor system 220. Position sensor system 220 may use any appropriate sensing technology or combination of sensing technologies, such as: OFDR (optical frequency domain reflectometry) techniques such as those using Fiber Bragg gratings, Raleigh scattering, or some other applicable reflection approach; position sensors enabled by EM (electromagnetic) techniques; linear rotary encoder techniques supported by capacitive, optical, resistive, or other technologies; etc. As a specific example, position sensor system 220 may comprise of, or be a component of, an EM sensor system with positional sensor system 220 including one or more conductive coils that may be subjected to an externally generated electromagnetic field. Each coil of such an EM sensor system used to implement position sensor system 220 then produces an induced electrical signal having characteristics that depend on the position and orientation of the coil relative to the externally generated electromagnetic field. In some implementations, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some implementations, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors used in some implementations of position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some implementations. In some implementations, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various implementations, medical instrument 226 is a biopsy instrument, which may be used to remove sample tissue or a sampling of cells from a target anatomic location. Medical instrument 226 may be used with an image capture probe also within flexible body 216. In various implementations, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 218. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In implementations in which medical instrument system 200 is actuated by a teleoperational assembly, drive unit 204 may include drive inputs that removably couple to and receive power from drive elements, such as actuators, of the teleoperational assembly. In some implementations, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some implementations, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562 (filed May 13, 2011, disclosing, "Medical System Providing Dynamic Registration of a Model of an Anatomic Structure for Image-Guided Surgery), which is incorporated by reference herein in its entirety.

In some examples, medical instrument system 200 may be teleoperationally controlled within medical system 100 of FIG. 1. In some implementations, manipulator assembly 102 of FIG. 1 may be replaced by direct operator control (e.g. non-teleoperationally controlled). In some implementations, manipulator assembly 102 may include assemblies which are teleoperationally controlled, assemblies which are robotically controlled, and/or assemblies which are manually controlled. In some examples, the direct operator control may include various handles and operator interfaces for hand-held operation of the instrument.

When using a teleoperational, robotic, or manual assembly to insert a catheter (or other elongate, flexible medical instrument) into a patient anatomy, the catheter length external to the patient should be supported as it is advanced into the patient. Otherwise, as the catheter is pushed from a proximal end and encounters friction in the patient anatomy at the distal end, the catheter may buckle or bend. To prevent this deformation of the catheter, an instrument guiding apparatus may be used to provide support to the catheter either continuously along the catheter length or at intervals as it enters the patient anatomy along an insertion axis. In some implementations, the instrument guiding apparatus may include a deployable tube through which the catheter may extend. In some implementations, the deployable tube may be maintained in tension to provide a sufficient level of stability and rigidity to the tube to support the catheter. In some implementations, the deployable tube may be formed of a flexible sheet coiled about a spool. The deployable tube may be in a laterally unfurled condition in an undeployed state, and a tubular condition having a lumen when in the deployed state. Generally, the catheter is introduced into the guiding apparatus while the apparatus is in a compressed configuration. After a distal portion of the catheter is disposed through a distal portion of the guiding apparatus, the guiding apparatus can be expanded or deployed about the remainder of the catheter. The instrument guiding apparatus returns to an un-deployed configuration as the catheter is advanced into the patient anatomy and the exposed length of the catheter decreases. As the catheter enters the patient anatomy, the guiding apparatus may roll about a spool. In some implementations, the instrument guiding apparatus described herein effectively provide stable support to the catheter as it is introduced into, traverses through, and is removed from the patient anatomy.

Figure 3:
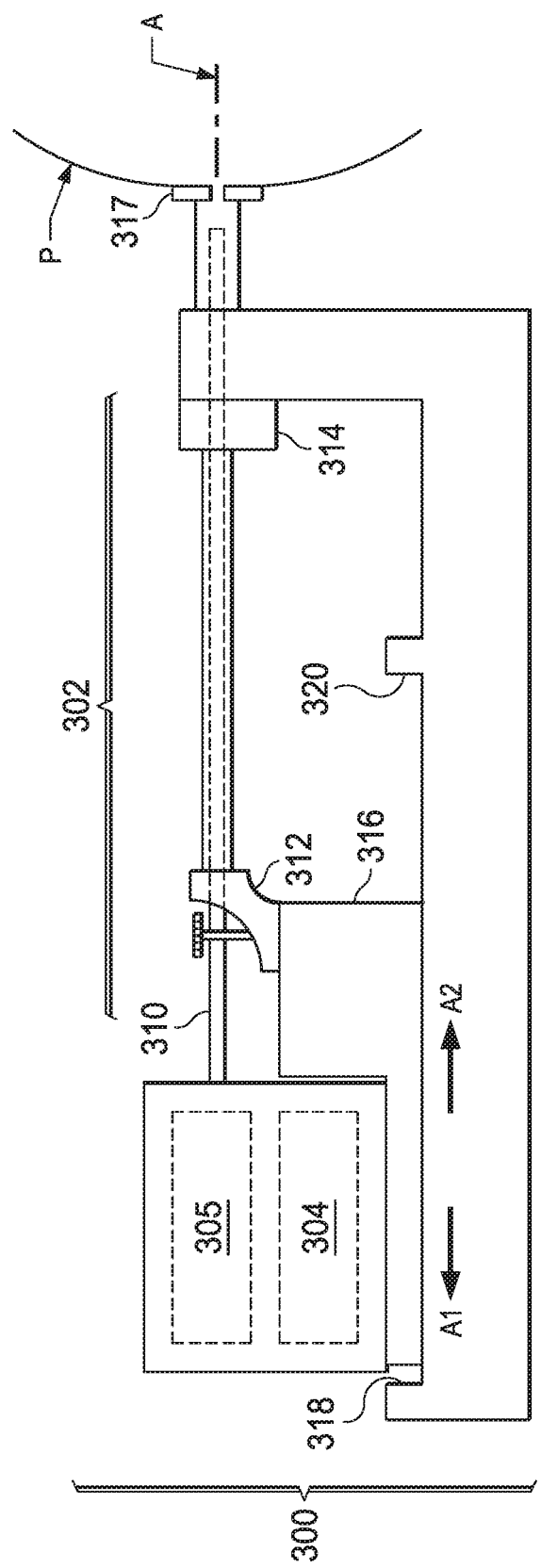
FIG. 3 is a simplified diagram of a side view of a manipulator assembly, an elongate instrument, and an instrument guiding apparatus according to some implementations of the present invention.

FIG. 3 diagrammatically illustrates an instrument interface portion 300 of a manipulator assembly (e.g., manipulator assembly 102) and an instrument guiding apparatus 302 according to an implementation of the present invention. The instrument interface portion 300 includes drive inputs 304 that may provide mechanical coupling of the instrument end effector and flexible body steering mechanism to the drive motors mounted to the manipulator. For example, a pair of drive inputs 304 may control the pitch motion of the distal end of the elongate flexible body (216 in FIG. 2A), with one adaptor of the pair controlling motion in the upward direction and the other of the pair controlling motion in the opposite downward direction. Other pairs of drive inputs 304 may provide opposing motion in other degrees of freedom for the flexible body and/or the end effector. In some implementations, the drive inputs 304 may be coupled to or positioned within an instrument control unit 305, which controls the positioning of an elongate instrument such as a catheter 310. Instrument interfacing with teleoperational or robotic manipulators is described, for example in U.S. Pat. No. 6,331,181 (filed Oct. 15 1999, disclosing "Surgical Robotic Tools, Data Architecture, And Use") and U.S. Pat. No. 6,491,701 (filed Jan. 12, 2001 disclosing "Mechanical Actuator Interface System For Robotic Surgical Tools) which are both incorporated by reference herein in their entirety. The instrument interface portion 300 may also control instrument insertion by moving linearly along an insertion axis A.

During use, the catheter 310 is positioned within the instrument guiding apparatus 302 and the instrument guiding apparatus 302 acts to minimize the buckling of the catheter 310 as the catheter 310 advances toward, remains within, and/or retracts from the patient anatomy. The instrument guiding apparatus 302 has a proximal end 312 and a distal end 314. In some implementations, the proximal end 312 of the instrument guiding apparatus 302 is detachably coupled to a mounting plate 316 of the instrument interface portion 300. The mounting plate 316 may be moveable (e.g., along the insertion axis A) relative to a proximal end 318 and a distal end 320 of the instrument interface portion 300. The proximal end 318 and the distal end 320 may or may not be disposed at the physical ends of the instrument interface portion 300. For example, in the pictured implementation, the proximal end 318 and the distal end 320 comprise motion stops disposed away from the actual ends of the instrument interface portion 300 that are shaped and configured to halt the axial translation of the mounting plate 316. During use, the distal end 314 of the instrument guiding apparatus 302 may be detachably coupled to an anchor 317 within the surgical field. The anchor 317 may be positioned on the instrument interface portion 300 (e.g., on a flexible instrument manipulator or FIM), the surgical table, on a surgical frame, or on the patient anatomy. In one example, the anchor 317 may comprise a mouth guard clamped by patient's teeth. The instrument guiding apparatus 302 provides longitudinal support along the length of the catheter 310 positioned within the instrument guiding apparatus 302 to minimize buckling of the exposed length of the catheter 310 as it is pushed into the patient's body P.

Figure 4:
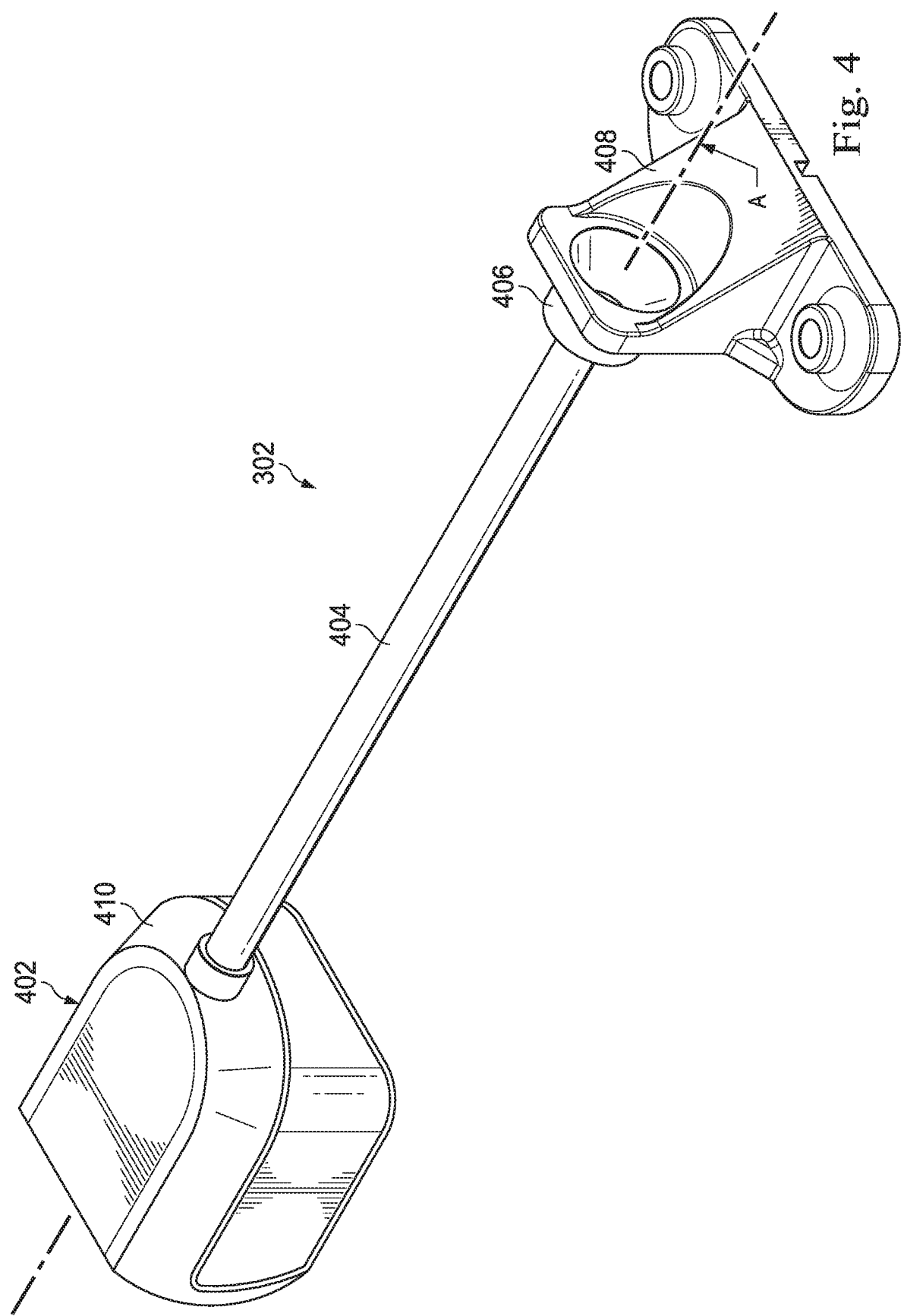
FIG. 4 is a perspective view of a diagram of an instrument guiding apparatus in a deployed tubular condition according to some implementations of the present disclosure.

FIGS. 4-12 illustrate various views of the exemplary instrument guiding apparatus 302 according to one implementation of the present disclosure. In particular, FIG. 4 illustrates a perspective view of the instrument guiding apparatus 302 in a deployed tubular condition. Referring to FIG. 4, the instrument guiding apparatus 302 includes a distal mount 402, a flexible sheet 404 shown in a deployed tubular condition, a proximal attachment element 406, and a proximal mount 408. In the implementation shown, the distal mount 402 comprises an outer housing 410 having a hollow cavity containing elements of the distal mount 402.

Although described herein as having the housing with elements of the distal mount 402 (described below) at the distal portion of the instrument guiding apparatus 302, other implementations are reversed so that the housing and its contents are disposed at the proximal portion of the instrument guiding apparatus 302. In such embodiments, the component forming the proximal attachment element 406 in FIG. 4 may be disposed at the distal portion of the instrument guiding apparatus 302. When the instrument guiding apparatus 302 is arranged as shown in FIG. 4, with the outer housing and its contents at the distal portion, the catheter 310 may advance and retract without moving the catheter relative to the support wall. However, when reversed so that the housing and its contents are disposed at the proximal portion, the housing may be closer to the surgical components, which may also provide some advantages.

Figure 5:
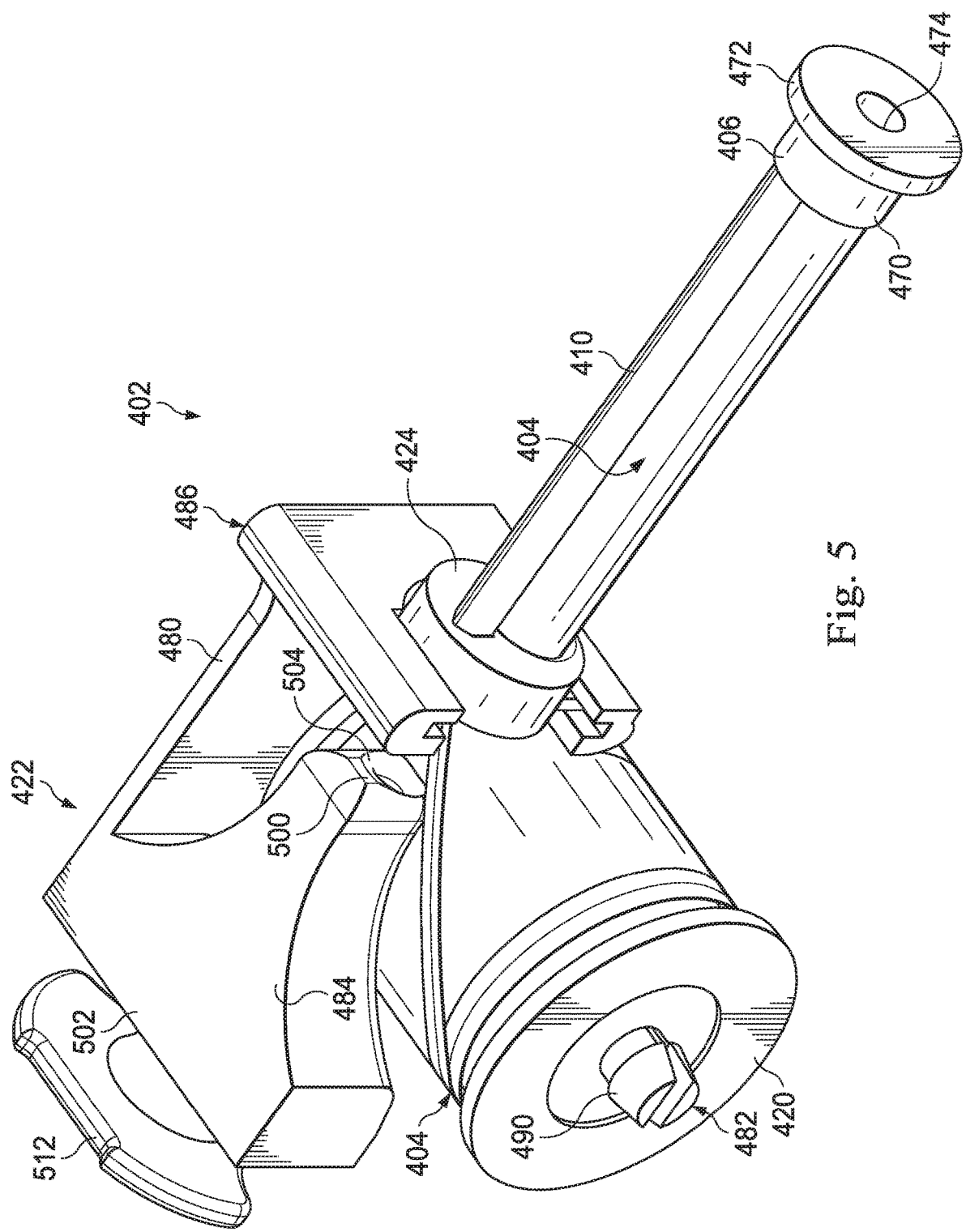
FIG. 5 is a perspective view of a diagram of a portion of the instrument guiding apparatus in a partially deployed tubular condition according to some implementations of the present disclosure.
Figure 6:
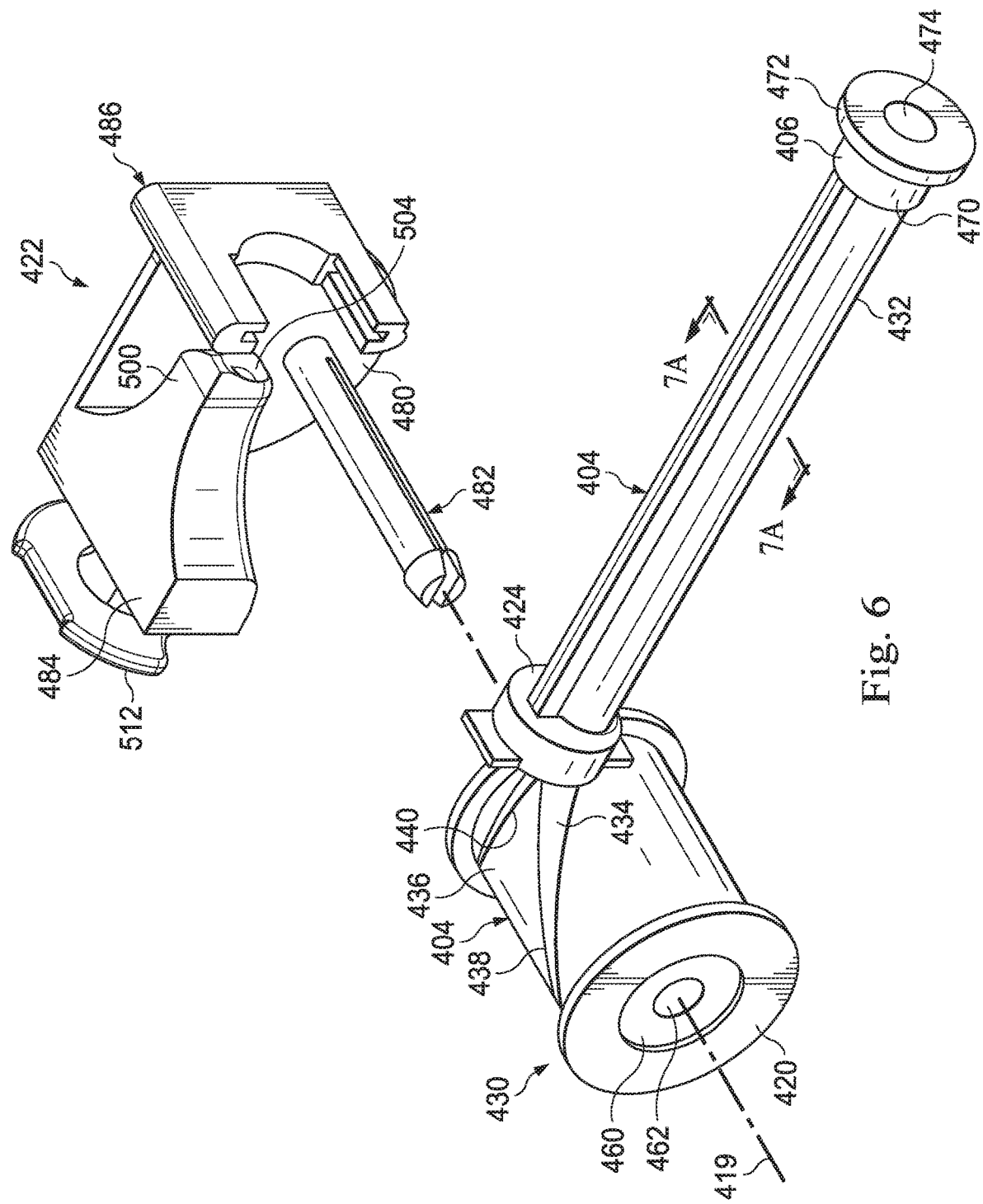
FIG. 6 is a perspective view of the portion of the instrument guiding apparatus of FIG. 5 in a partially exploded configuration according to some implementations of the present disclosure.

FIG. 5 illustrates a perspective view of a portion of the instrument guiding apparatus 302 in a partially deployed tubular condition. In FIG. 5, the outer housing 410 of the distal mount 402 is removed to show additional components of the instrument guiding apparatus 302. In addition, in FIG. 5, the proximal mount 408 is also removed to more fully show the proximal attachment element 406. In FIG. 5, the distal mount 402 also includes a spool 420 about which the flexible sheet 404 may wrap when in a laterally unfurled condition, a spool guide 422 that may aid in separating the flexible sheet 404 when the flexible sheet moves from the deployed tubular condition to the laterally unfurled condition and may aid in aligning the flexible sheet 404 when the flexible sheet moves from the laterally unfurled condition to the deployed tubular condition, and a slide fastener 424 that may be disposed to connect and disconnect lateral margins of the flexible sheet 404 in a manner described herein. FIG. 6 illustrates the components of FIG. 5 in a partially exploded configuration, showing the spool 420 and the spool guide 422 in an unassembled condition, while maintaining the slide fastener 424 about the flexible sheet 404.

In the implementations described herein, the spool 420, the spool guide 422, and the slide fastener 424 cooperate to deploy the flexible sheet 404 from the laterally unfurled condition to the deployed tubular condition. FIGS. 5, 6, 7A, and 7B show a portion of the flexible sheet 404 in the laterally unfurled condition and also shows a portion of the flexible sheet 404 in the deployed tubular condition. The flexible sheet 404 includes a distal portion 430 and a proximal portion 432. In this implementation, the flexible sheet 404 includes two opposing lateral margins, referenced herein as lateral margin 434 and lateral margin 436, extending the length of the flexible sheet 404 from the distal portion 430 to the proximal portion 432. The lateral margin 434 includes a face 437 formed of a portion of the surface of the lateral margin 434 and also includes a peripheral edge 438. Likewise, the lateral margin 436 includes a face 439 formed of a portion of the surface of the lateral margin 436 and also includes a peripheral edge 440. As used herein, the term lateral margin includes the region of material extending along the lateral edges of the flexible sheet. In some examples, each lateral margin may extend from the peripheral edge to about 20% of the width of the flexible sheet. In other examples, each lateral margin may extend from the peripheral edge to about 40% of the width of the flexible sheet.

Figure 7A:
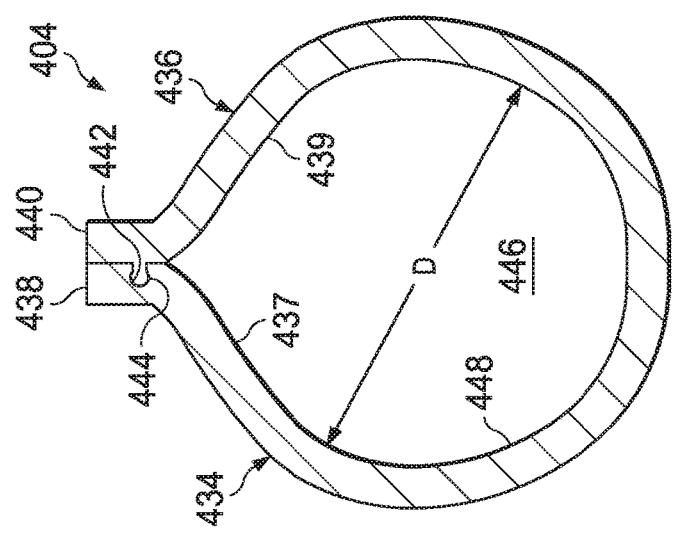
FIG. 7A is a cross-sectional diagram of a sheet material in a deployed tubular condition and usable with the instrument guiding apparatus of FIG. 5 according to some implementations of the present disclosure.
Figure 7B:
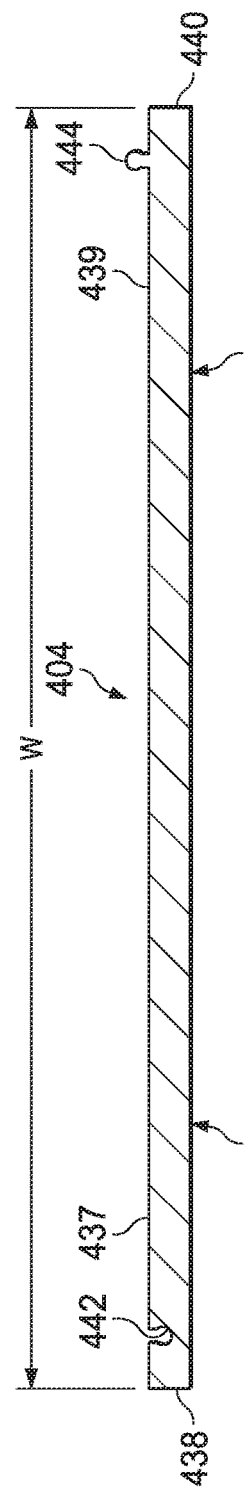
FIG. 7B is a cross-sectional diagram of a sheet material in a laterally unfurled condition and usable with the instrument guiding apparatus of FIG. 5 according to some implementations of the present disclosure.

FIGS. 7A and 7B show the flexible sheet 404 in a deployed tubular condition and a laterally unfurled condition, respectively. FIG. 7A, showing the deployed tubular condition, is a cross-section taken along lines 7A-7A in FIG. 6. FIG. 7B, showing the laterally unfurled condition, is a cross-sectional view representing the condition in which the flexible sheet 404 may be disposed when wound around the spool 420 in FIGS. 5 and 6. In the implementation shown, the lateral margin 434 and the lateral margin 436 each includes cooperating coupling structures, referenced as fastener portions. For example, the lateral margin 434 includes a fastener portion 442, and the lateral margin 436 includes a fastener portion 444. In this example, the fastener portion 442 is shown as a pocket or groove formed in the face the 437 of the lateral margin 434. The pocket or groove may extend substantially parallel to the peripheral edge 438 along the length of the flexible sheet 404. For example, it may extend from the distal portion 430 of the flexible sheet 404 to the proximal portion 432 of the flexible sheet 404. The fastener portion 444 is shown in this example as a protrusion may extend substantially parallel to the peripheral edge 440 along the length of the flexible sheet 404, and may extend from the distal portion 430 to the proximal portion 432 of the flexible sheet 404. When the flexible sheet 404 is in the laterally unfurled condition shown in FIG. 7B, the fastener portion 442 and the fastener portion 444 are laterally separated from each other. However, when the flexible sheet 404 is in the deployed tubular condition, the fastener portion 442 may interlock with the fastener portion 444 to selectively couple the lateral margin 434 to the lateral margin 436. In this manner, the fastener portions 442, 444 may function as an interlocking zipper extending the length of the flexible sheet. Although described and shown as a groove and protrusion in the implementation shown, it is contemplated that other fastener portions may be employed to connect the lateral margin 434 to the lateral margin 436. Some examples include multiple interlocking protrusions. For example, some embodiments may use protrusions such as teeth, may use buttons, snaps, hook and loop fasteners, mushroom cap type reclosable fasteners (such as DUAL LOCK™ reclosable fasteners), or other fastener portions, interlocking or non-interlocking, that may connect by being pressed together, or may be meshed together to form a zipper. In some implementations, the fastener portions are conventional zippers that connect the opposing lateral margins to form the tubular shape. In some implementations, the fastener portions may include bonding agents such as adhesives that selectively adhere when touching, but may be selectively separated so that the flexible sheet 404 may be disposed in the laterally unfurled condition or the deployed tubular condition.

The flexible sheet may be formed of any flexible material suitable for forming a lumen that may sufficiently provide lateral support to an elongated flexible surgical instrument, such as a flexible catheter to prevent or minimize buckling of the catheter as it is advanced into a patient. In some implementations, the flexible sheet may be a fabric, a polymer, or other flexible material. In some implementations, the flexible sheet is formed of a single-piece, extruded flexible sheet of PET, LDPE, and HDPE, although other flexible materials are contemplated. In some implementations, the flexible sheet is PET having a 0.127 mm thickness. Both thicker and thinner thicknesses are contemplated. In some implementations, the flexible sheet is formed of multiple materials, sewn, welded, bonded, glued, adhered or otherwise attached to each other. In some implementations, the lateral margins including the fastening portions may be sewn or attached to opposing edges of a flexible sheet.

When in the deployed tubular condition, the flexible sheet 404 forms a lumen 446. When used as the instrument guiding apparatus 302, the lumen 446 includes an inner surface 448 surrounding the catheter 310 (FIG. 3). The inner surface 448 may provide lateral support to the catheter 310 to prevent buckling or bending as the catheter advances toward or into the patient. In order to provide support, in some implementations the diameter D of the guiding apparatus 302, represented by the flexible sheet 404 in a deployed tubular condition, may be in a range of about 2 mm to about 20 mm. In some implementations, the guiding apparatus 302 may have a diameter D in a range of about 2 mm to 10 mm, and in some implementations, may have a diameter D in a range of about 3 mm to 5 mm. Both larger and smaller diameters are contemplated, and the diameter may be selected based on the diameter of the catheter to be supported and may take into account the rigidity or flexibility of the catheter. The width W of the flexible sheet 404 may be selected to provide the desired diameter, and in some embodiments, may be about 63 mm or less to provide a diameter of about 20 mm or less. In some implementations, additional width may be required to compensate for overlap of portions of the lateral margins 434, 436. It is contemplated that the width W may be larger or smaller than described in the example herein.

Returning now to FIGS. 4-6, and as described above, when in use, the distance between the distal mount 402 and the proximal mount 408 decreases as the catheter 310 is advanced by the instrument interface portion 300. Therefore during this period of time, the portion of the flexible sheet 404 in the deployed tubular condition is gradually converted to the laterally unfurled condition by separating the fastener portions 442, 444 and winding the flexible sheet 404 about the spool 420. Likewise, when the distance between the distal mount 402 and the proximal mount 408 increases as the catheter is withdrawn by the instrument interface portion, the flexible sheet in the laterally unfurled condition is unwound from the spool and folded to form the deployed tubular condition and the fastener portions 442, 444 are connected together to create the lumen 446, through which the catheter 310 extends.

FIGS. 6 and 8 show the spool 420 independent of the spool guide 422 with the flexible sheet 404 disposed thereon. In the implementation shown, the spool 420 includes a body 460 constructed to form a central hole 462 disposed therein, which may define a rotation axis 419 for the spool 420 when it winds the flexible sheet 404. In some implementations, the spool 420 includes or cooperates with spooling mechanism that provides a winding force on the flexible sheet 404. In some implementations, the spooling mechanism is or includes a biasing element 464 (FIG. 8), such as a spring. Because of the biasing element of spooling mechanism, the spool 420 may be subject to a biasing force that automatically and continuously retracts and winds the flexible sheet 404. Depending on the implementation, the biasing element 464 may include a spring reel, a constant force spring, or other spring. The spooling mechanism may be selected to overcome friction and other drag forces while still providing sufficient force to reel in or roll the flexible sheet 404 to a rolled configuration, and in some implementations, to provide continuous tension to the tubular portion of the flexible sheet 404 to create rigidity for stabilization of the catheter. In some implementations, the spooling mechanism may be an electric motor, such as a servo motor or other rotary or linear actuator that may apply a force to roll the spool 420. In some implementations, the spooling mechanism is formed as a part of the spool 420. In other implementations, the spooling mechanism is disposed as a part of the outer housing 410 (FIG. 4), which may engage the spool 420 and apply the biasing winding force. For example, some implementations of the spooling mechanism include a gear on a lateral side of the spool 420 that may engage a gear on the housing, with the gear on the housing being biased via the biasing element to apply a rolling force to the spool 420. The central hole 462 may be circular or noncircular depending on the implementation. In some implementations, noncircular central holes 462 in the spool 420 may engage or be rotated by corresponding noncircular shafts or mandrels biased by the biasing element 464.

Both FIGS. 6 and 8 also include the proximal attachment element 406. The attachment element 406 may be a flanged fitting having a body 470 and a flange 472 with a central passage 474 therethrough sized to permit passage of the catheter 310. Although the flexible sheet 404 may be attached in any manner to the proximal attachment element 406, in some implementations, the flexible sheet 404 is adhered via a bonding agent, such as an adhesive to the body 470. The flange 472 may be disposed at the proximal end of the body and may be shaped and sized to attach to the proximal mount 408. Depending upon the implementation, the flange 472 may slide into a notch that securely holds the flange 472 in place. In this manner, the proximal attachment element 406 may be secured to the proximal mount. Furthermore, some implementations include the proximal mount 408 as integral with the proximal attachment element 406.

Figure 9:
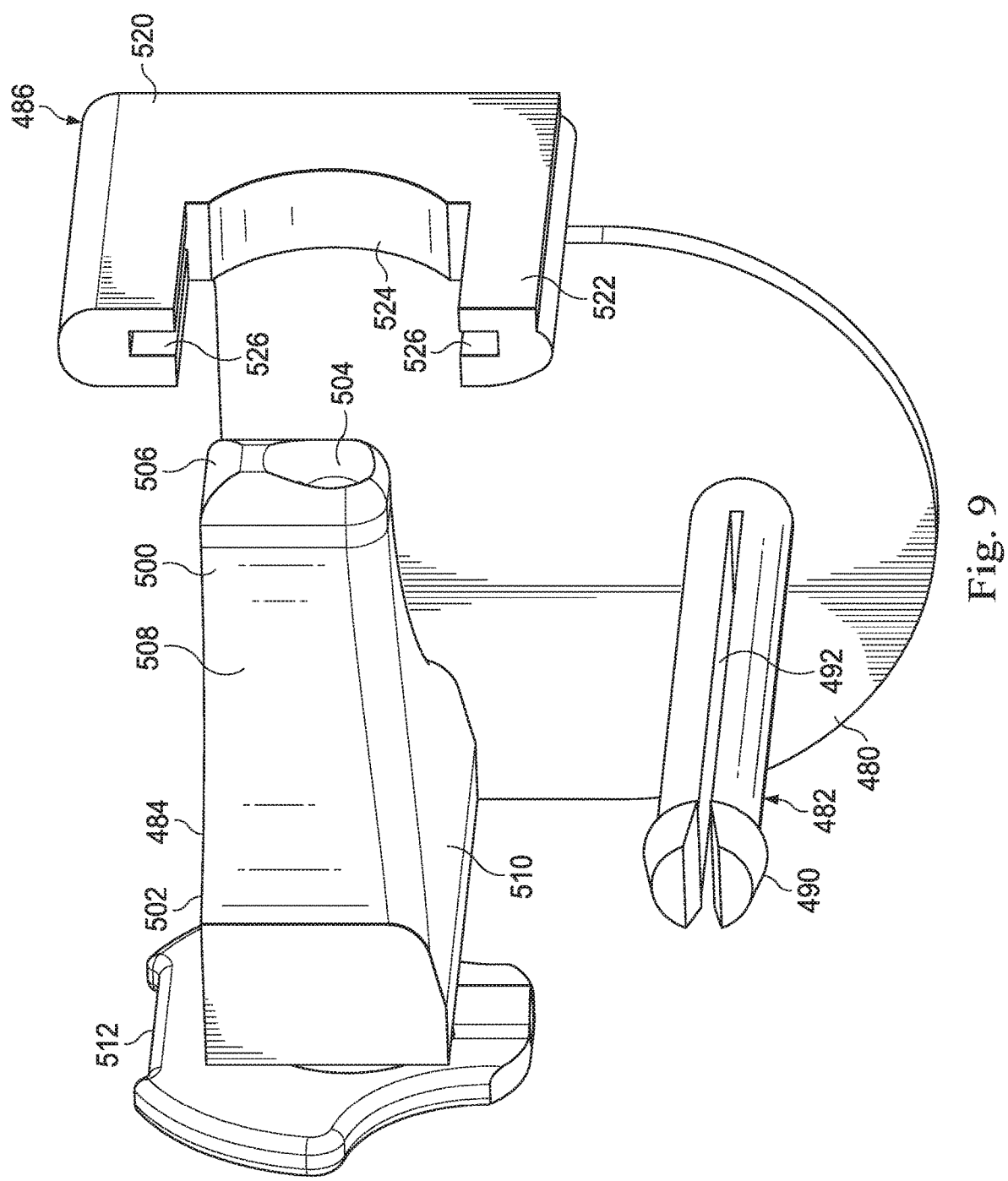
FIG. 9 is a perspective view of a diagram of a spool guide forming a part of the instrument guiding apparatus of FIG. 5 according to some implementations of the present disclosure.

FIGS. 5, 6, and 9 show the spool guide 422. In the implementation shown, the spool guide 422 includes a stabilizing base 480, a mandrel 482, an introducer/splitter 484, and a slide mount 486. The stabilizing base 480 provides support and spatial alignment to the mandrel 482, the introducer/splitter 484, and the slide mount 486. In the embodiment shown, the stabilizing base 480 is implemented as a wall but may also form an inner wall of the outer housing 410 or other support. In some implementations, the spool guide 422 may also include the biasing element that may bias the spool 420 to a retracted or wound condition.

The mandrel 482 may extend laterally from the stabilizing base 480 and may be sized to fit into the central hole 462 of the spool 420. In the implementation shown, the mandrel 482 is a cylindrical shaft having a bulbous end 490. An axial slot 492 may allow elastic, radial compression of the mandrel 482 as the mandrel 482 is introduced into the central hole 462 of the spool 420. After passing through the central hole 462, the mandrel 482 may elastically return to its prior form, the bulbous end 490 maintaining the spool 420 on the mandrel 482.

The introducer/splitter 484 operates to fold the flexible sheet 404 from the laterally unfurled condition to the deployed tubular condition, to unfold the flexible sheet 404 from the deployed tubular condition to the laterally unfurled condition and to introduce the catheter 310 into the lumen of the flexible sheet 404 when in the deployed tubular condition. Accordingly, the introducer/splitter 484 includes a relatively narrower leading portion 500, a wider trailing portion 502, and a through passage 504 extending therethrough. The leading portion 500 forms a protruding nose that interfaces with the flexible sheet 404 to fold or unfold the flexible sheet. In the embodiment shown, the leading portion 500 includes rounded edges between a front face 506 and side surfaces 508. A bottom surface 510 faces the mandrel 482 and may further smooth and maintain the flexible sheet 404 in the laterally unfurled condition when wrapped around the spool 420. In the implementation shown, the bottom surface 510 may be shaped with an arc to better accomplish its purpose.

The trailing portion 502 may have a width greater than the leading portion and in some instances has a width about the same width as the flexible sheet 404. An introducer mount 512 may be disposed at the trailing portion 502 and may assist in securing the introducer/splitter 484 or the spool guide 422 to the instrument interface portion 300.

The through passage 504 extends through the leading portion 500, through the trailing portion 502, and out the introducer mount 512. When the spool guide 422 is disposed at the distal end 314 of the instrument guiding apparatus 302, the catheter passes through the leading portion 500 and out the trailing portion 502 before entering the patient. Accordingly, the flexible sheet 404 in the deployed tubular condition supports the lateral sides of the catheter 310 as it advances into the through passage 504.

The slide mount 486 may extend from the stabilizing base 480 and may be disposed in front of the leading portion 500. The slide mount 486 may be arranged to secure the slide fastener 424 in place. In the embodiment shown, the slide mount 486 includes an upper support 520, a lower support 522, and a lateral side surface 524, together forming a C shape. The upper support 520 and the lower support 522 may each have receiving grooves 526 that allow lateral entry of the slide fastener 424. The slide mount is disposed so that the slide fastener is aligned with the through passage 504 of the introducer/splitter 484. In so doing, the axis defined by the through passage 504 may be coaxial with an axis of the lumen defined by the flexible sheet 404 when in the deployed tubular condition. Accordingly, the catheter 310 may be substantially aligned with this axis as it extends through the through passage 504 and the lumen of the flexible sheet 404.

Figure 10:
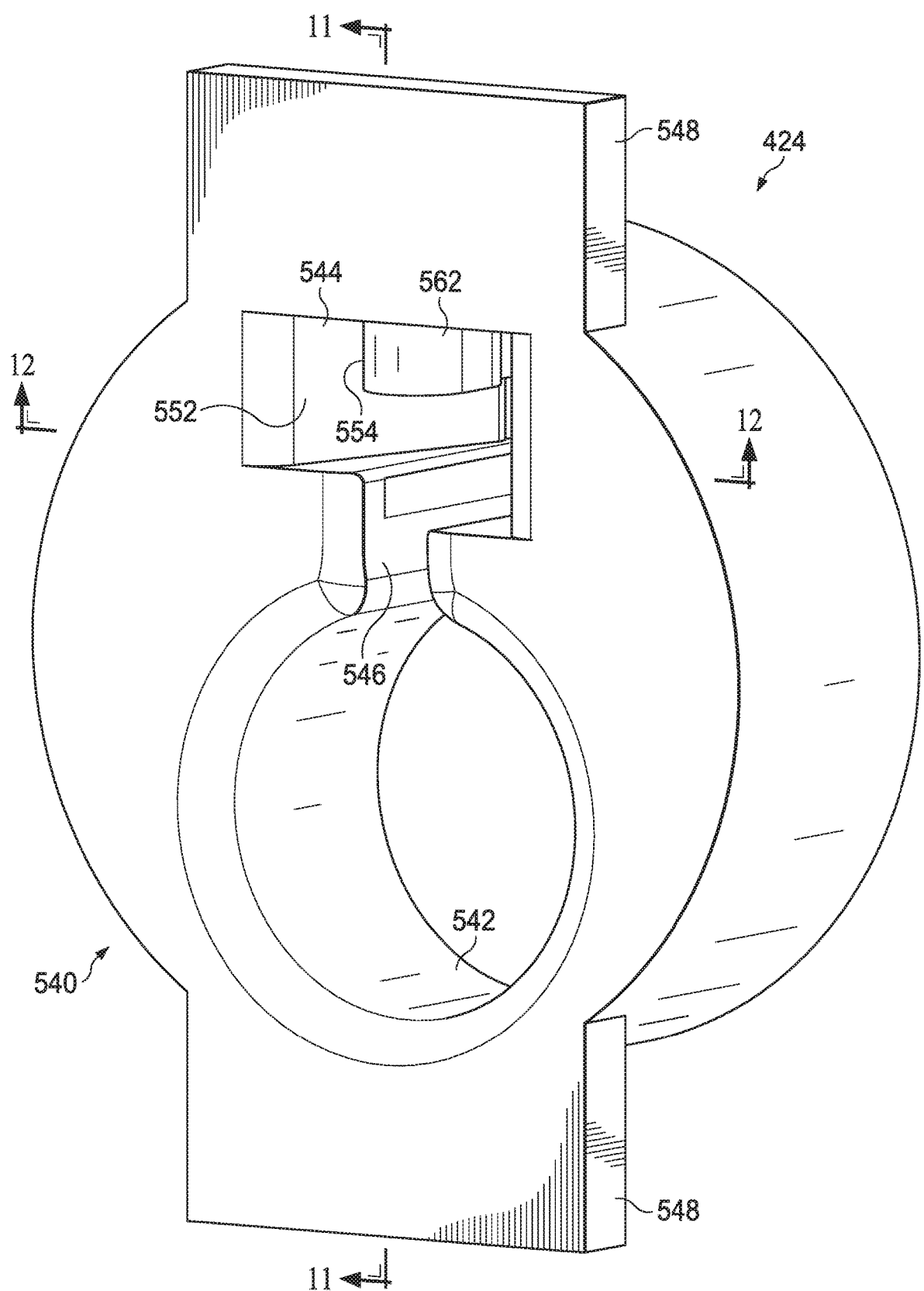
FIG. 10 is a perspective view of a diagram of a slide fastener forming a part of the instrument guiding apparatus of FIG. 5 according to some implementations of the present disclosure.
Figure 11:
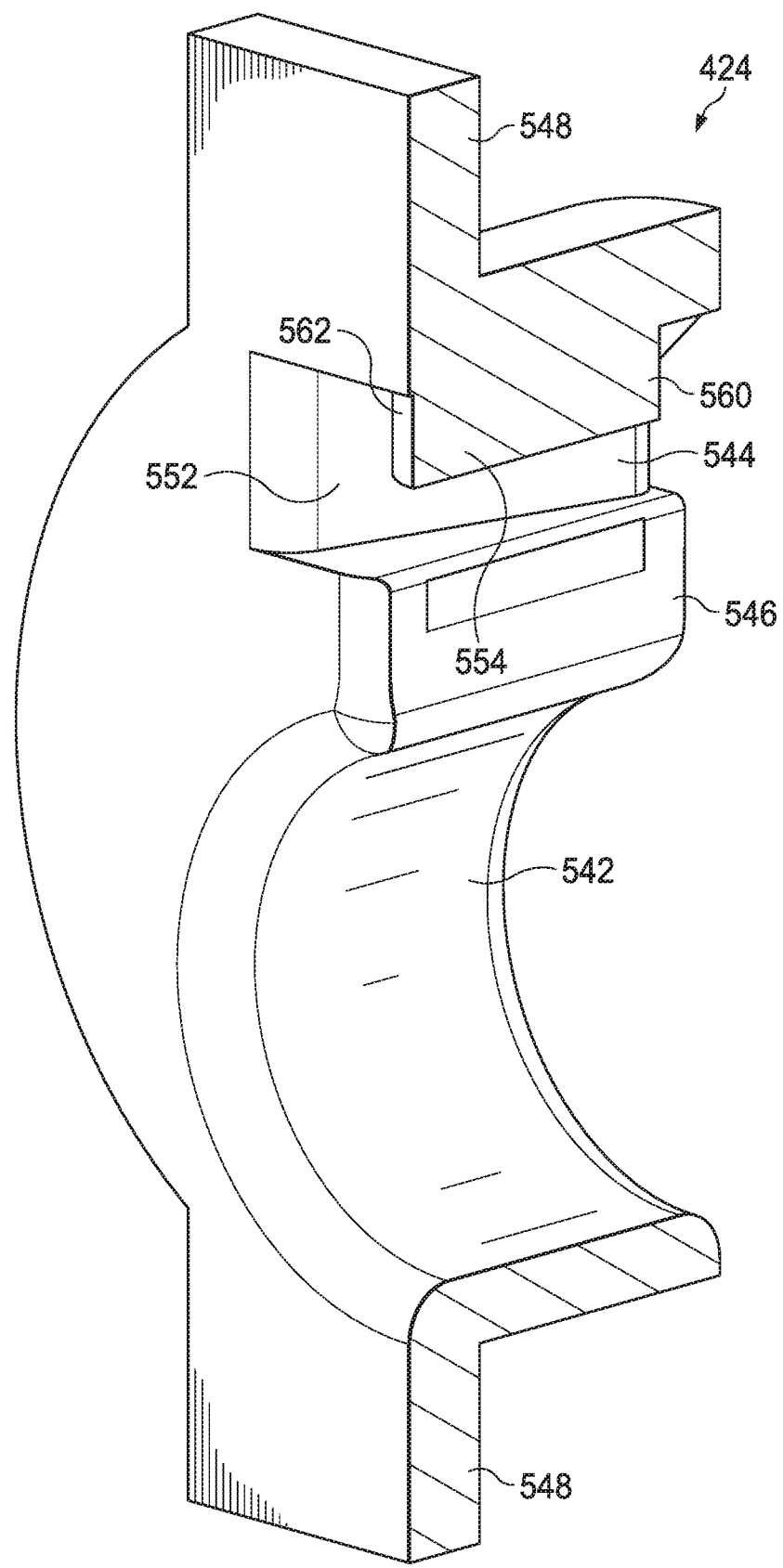
FIG. 11 is a cross-sectional diagram taken along lines 11-11 in FIG. 10 according to some implementations of the present disclosure
Figure 12:
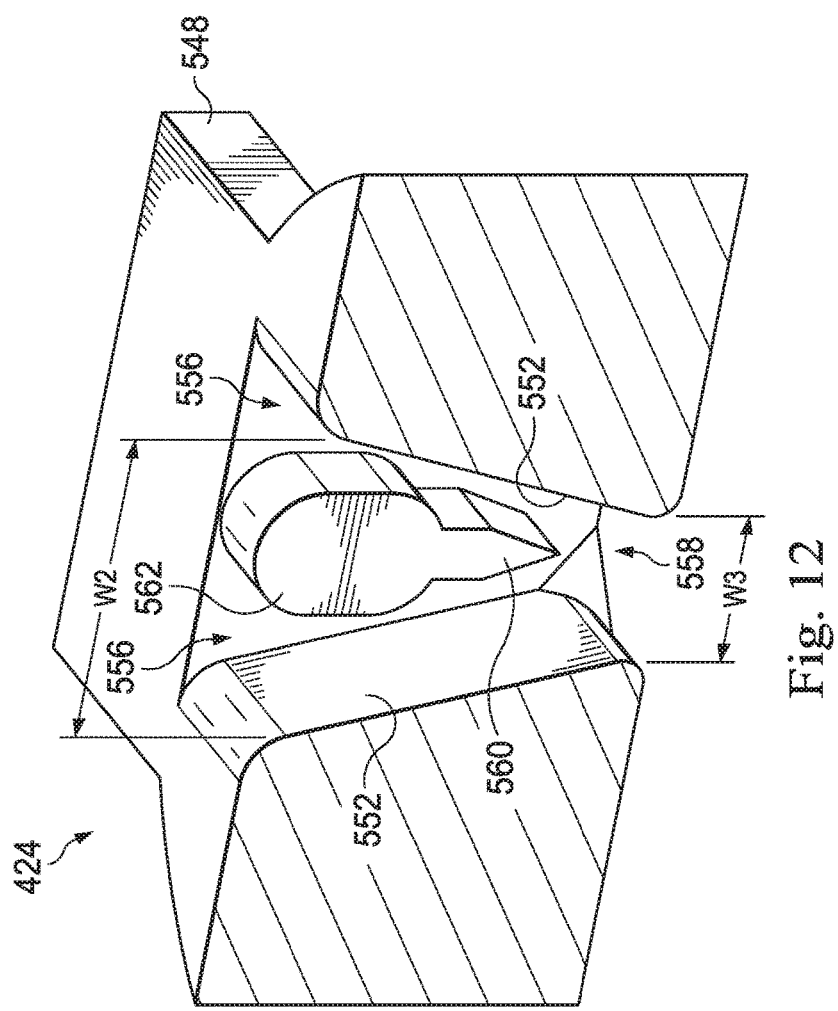
FIG. 12 is a cross-sectional diagram taken along lines 12-12 in FIG. 10 according to some implementations of the present disclosure.

FIGS. 10-12 show an implementation of the slide fastener 424. FIG. 10 shows a perspective view of the slide fastener 424, FIG. 11 shows a cross-sectional view taken along lines 11-11 in FIG. 10, and FIG. 12 shows a cross-sectional view taken along lines 12-12 in FIG. 10.

In the example shown, the slide fastener 424 is configured to couple and uncouple the cooperating coupling structures, referenced herein as fastener portions. In this implementation, the slide fastener 424 is a ring 540 with a main orifice 542, a zip slide orifice 544, separated by a neck 546. The ring 540 includes wings 548 extending therefrom. In this implementation, the wings 548 protrude from opposing sides of the ring 540. In some implementations, the wings 548 form a radial flange or other feature, the wings 548 are shaped and sized to fit within the grooves 526 of the slide mount 486 (FIG. 9) forming a part of the spool guide 422. In this embodiment although the ring 540 has a generally circular outer circumference, the ring 540 may be of any shape.

Furthermore, although the slide fastener 424 may be introduced to the slide mount 486, in other implementations, the slide fastener 424 may be an integral portion of the mount 486 or the spool guide 422. However, the implementation shown accommodates any of a plurality of slide fasteners that may be desired to be used with the spool guide 422. For example, different types of flexible sheets 404 with different types of fastener portions may be best utilized with different types of slide fasteners.

The main orifice 542 is in this embodiment, a circular orifice through which a central portion of the flexible sheet 404 may pass as the flexible sheet is deployed to the deployed tubular condition or retracted to the laterally unfurled condition. The zip slide orifice 544 is configured to receive portions of the lateral margins of the flexible sheet 404. The zip slide orifice 544 is shaped and arranged to drive the fastener portions 442, 444 together in a locked or coupled relationship, or alternatively to separate or uncouple the fastener portions 442, 444. The cross sectional view of FIG. 12 shows additional detail of the zip slide orifice 544. As can be seen, the zip slide orifice 544 includes opposing lateral walls 552 that taper toward and away from one another. As such, the zip slide orifice 544 includes an opening 556 on one side of the zip slide orifice 544 having a width W2, and an opening 558 on the opposing side of the zip slide orifice 544 having a width W3. A tongue 554 projects into the zip slide orifice 544. In this implementation, the tongue 554 is a boss having a height sufficient to separate or guide the lateral margins of the flexible sheet 404. In the implementation shown, the tongue 554 is relatively arrow shaped, with a narrow leading portion 560 and a wider trailing portion 562. The distance between the tongue 554 and the opposing lateral walls 552 may define a gap 564 that may be sized to permit passage of at least one of the fastener portions of the lateral margins. The neck 546 is narrower than the main orifice 542 and the zip slide orifice 544, but connects them both. Although described as opposing lateral walls 552, other implementations employ rollers that press together the fastener portions of the lateral margins.

In use, the flexible sheet 404 passes through the main orifice 542, the neck 546, and the zip slide orifice 544. The fastener portions 442, 444 of the lateral margins 434, 436 pass through the zip slide orifice 544. In some implementations, the fastener portions 442, 444 extend on opposing sides of the tongue 554. As the fastener portions pass through the zip slide orifice 544 in a zipping or coupling direction, the taper of the opposing lateral walls 552 compresses the fastener portions against one another, coupling them together. In some implementations, the fastener portions couple when a protrusion interlocks with a groove as described herein. In other implementations, the fastener portions couple using an intermittent interlocking relationship. In yet other implementations, the fastener portions operate as a zipper with teeth that mesh together. As the fastener portions 442, 444 pass through the zip slide orifice 544 in an unzipping or uncoupling direction, the leading edge of the tongue 554 causes the fastener portions 442, 444 to separate from one another, allowing the flexible sheet 404 to transition from the deployed tubular condition to the laterally unfurled condition.

Figure 13A:
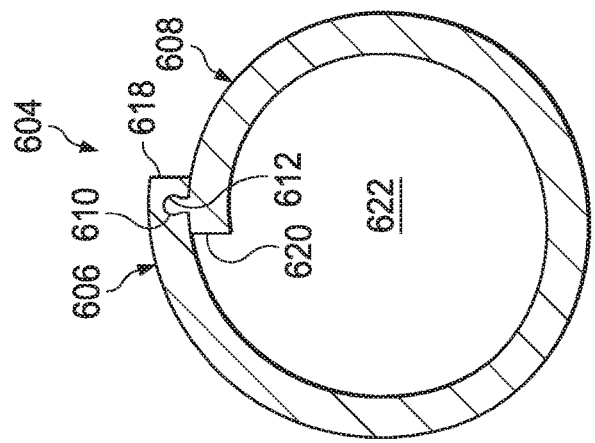
FIG. 13A is a cross-sectional diagram of a sheet material in a deployed tubular condition and usable with the instrument guiding apparatus of FIG. 5 according to some implementations of the present disclosure.
Figure 13B:
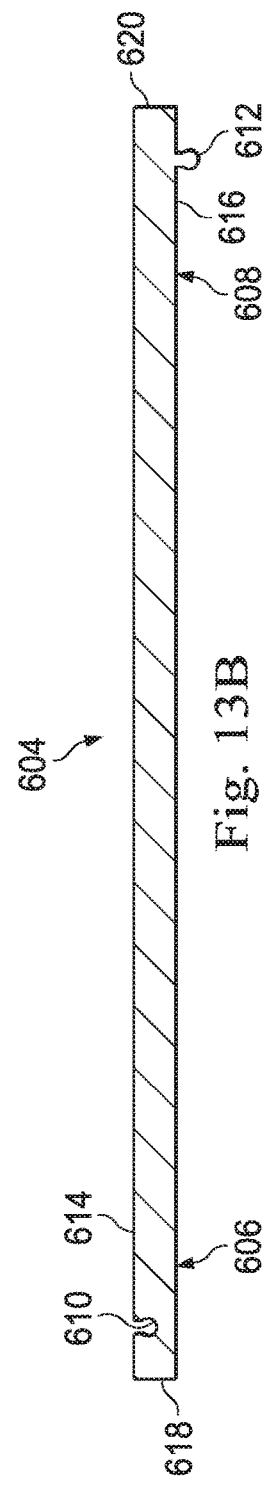
FIG. 13B is a cross-sectional diagram of a sheet material in a laterally unfurled condition and usable with the instrument guiding apparatus of FIG. 5 according to some implementations of the present disclosure.

FIGS. 13A and 13B show another implementation of a flexible sheet, referenced by the numeral 604. FIG. 13A shows the flexible sheet 604 in a deployed tubular condition and FIG. 13B shows the flexible sheet 604 in a laterally unfurled condition. The flexible sheet 604 includes a lateral margin 606 and a lateral margin 608. The lateral margin 606 includes a fastener portion 610, and the lateral margin 608 includes a fastener portion 612. The fastener portion 610 is shown as a pocket or groove formed in a face 614, and the fastener portion 612 is shown as a protrusion formed in a face 616. As described above with reference to flexible sheet 404, the fastener portion 610, 612, may extend substantially parallel to respective edges 618, 620 along the length of the flexible sheet 604. In this implementation, the fastener portion 612 is disposed on an opposing side of the flexible sheet 604. As shown in FIG. 13A, when in the deployed tubular condition, the lateral margins 606, 608, overlap and may selectively couple together such as by interlocking, to form an enclosed lumen 622. The flexible sheet 604 may be used with the instrument guiding apparatus 302 in the manner described above. Additional details and features of the sheet 604 may be the same as or similar to the additional details and features of the sheet 404 described herein. For simplicity, they will not be repeated here.

Figure 14A:
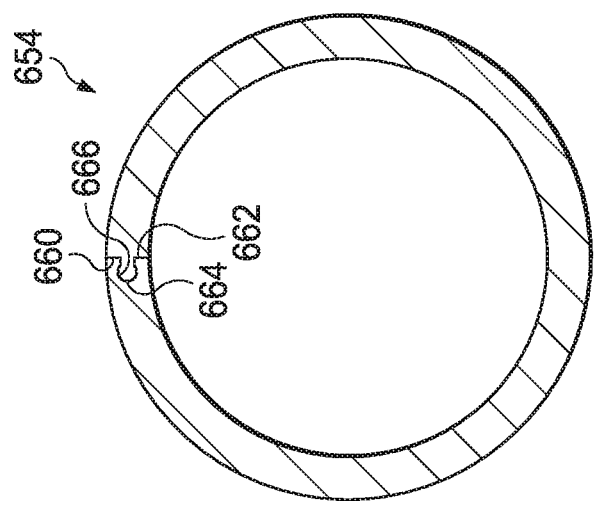
FIG. 14A is a cross-sectional diagram of a sheet material in a deployed tubular condition and usable with the instrument guiding apparatus of FIG. 5 according to some implementations of the present disclosure.
Figure 14B:
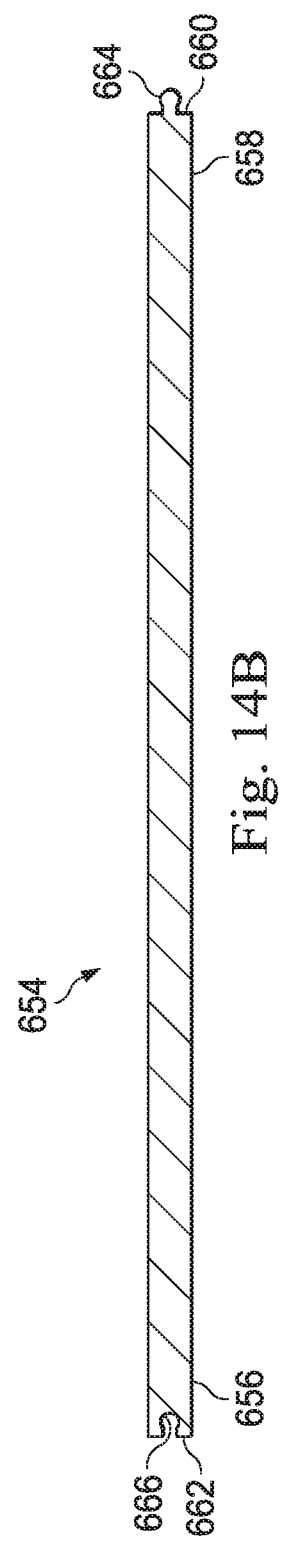
FIG. 14B is a cross-sectional diagram of a sheet material in a laterally unfurled condition and usable with the instrument guiding apparatus of FIG. 5 according to some implementations of the present disclosure.

FIGS. 14A and 14B show yet another implementation of a flexible sheet referenced by the numeral 654, with the flexible sheet 654 shown in the deployed tubular condition in FIG. 14A and in the laterally unfurled condition in FIG. 14B. In this implementation, the flexible sheet 654 includes lateral margins 656, 658. Each lateral margin 656, 658 includes a respective peripheral edge 660, 662. Each peripheral edge 660, 662 includes a fastener portion, referenced herein as 664, 666. When the flexible sheet 654 is in the deployed tubular condition of FIG. 14A, the fastener portion 664, 666 are coupled together in the manner described herein. This implementation shows an edge to edge connection, in contrast to the face-to-face connection shown in FIGS. 7A, 7B, 13A, and 13B. Yet other embodiments may include an end-to-face connection. Additional details and features of the sheet 644 may be the same as or similar to the additional details and features of the sheet 404 described herein, and will not be repeated here.

The systems and methods of this disclosure are suited for use in the connected bronchial passageways of the lung, as well as for navigation and treatment of other tissues, via natural or surgically created connected passageways, in any of a variety of anatomical systems including the colon, the intestines, the kidneys, the brain, the heart, the circulatory system, the reproductive system, or the like. The methods and implementations of this disclosure are also suitable for non-interventional applications.

In use, the instrument guiding apparatus 302 may be used to provide lateral support to a flexible catheter 310 as it is advanced toward a patient. Because of its configuration, a tube may be formed or deployed about the catheter as the catheter axially displaces on one direction, and likewise, the tube may be undone or removed from about the catheter as the catheter axially displaces in the other direction. As described herein, the catheter may be fixed in position relative to the proximal mount 408. In some implementations, the proximal mount 408 of FIG. 4 may be disposed adjacent the distal mount 402, and the catheter may be introduced through the distal mount and the proximal mount. With the catheter fixed relative to the proximal mount, the catheter and proximal mount may be axially displaced to separate the proximal mount from the distal mount. As this occurs, the instrument guiding apparatus deploys the flexible sheet to form a tube at the distal mount to continuously cover and protect the catheter, even as the proximal mount moves away from the distal mount. Because the flexible sheet is maintained in tension via the biasing element on the spool, the flexible sheet in the deployed tubular condition has sufficient rigidity to provide lateral support to the flexible catheter. That is, in some implementations, the tension in the flexible sheet provides rigidity to support the catheter.

During the surgical procedure, the proximal mount 408 may advance toward the distal mount 402 to move the catheter through the distal mount and toward or into a patient. As this occurs, the flexible sheet is deformed from the deployed tubular condition to the laterally unfurled condition, permitting the catheter to exit the lumen of the flexible sheet in the deployed tubular condition, pass through the spool guide 422, and into the patient.

It is worth noting that in some implementations, the material of the flexible sheet may be chosen to provide rigidity in a tubular form sufficient to support desired lateral loading for any of a variety of purposes. For example, more rigid materials may be used to support structures independent of tension on the material. For example, the deployable tube may be used to form a deployable boom having lateral stiffness even when unanchored at one of the distal and proximal ends. Such systems may be used in tripods, selfie-sticks, microphone stands, or other systems conventionally employing telescoping or collapsing rods. In some examples, the deployable tube may be used to transport or flow fluids, either liquid or gas. In such systems, the fastener portions may be selected to provide a leak-proof seal extending the length of the deployed portion. In other examples, the deployable tube may be used in Biologics to isolate or to contain biological materials. Such systems may use complete shielding to separate the outside environment from the environment within the lumen. The unzipping and zipping nature of the deployable tube may find additional uses in, without limitation, aerospace, healthcare, aviation, oil and gas, and other industries.

While certain exemplary implementations of the invention have been described and shown in the accompanying drawings, it is to be understood that such implementations are merely illustrative of and not restrictive on the broad invention, and that the implementations of the invention not be limited to the specific constructions and arrangements shown and described, since various other modifications may occur to those ordinarily skilled in the art.

What is claimed is:

1. A deployable tube apparatus including a first end and a second end, the deployable tube apparatus comprising:
a spool at the second end; and
a flexible sheet coiled about the spool in a laterally unfurled condition and having a first lateral margin and a second lateral margin, the flexible sheet being deployable from the laterally unfurled condition with the first and the second lateral margins spaced from each other to a deployed tubular condition where the first and the second lateral margins are coupled to each other to form an enclosed lumen, wherein the flexible sheet extends from a proximal attachment element at the first end of the deployable tube apparatus to the spool at the second end of the deployable tube apparatus.

2. The deployable tube apparatus of claim 1, comprising a fastener portion arranged to selectively fasten the first and the second lateral margins.

3. The deployable tube apparatus of claim 2, comprising a guide that selectively fastens and unfastens the fastener portion when said at least one of the first and the second lateral margins displaces past the guide, the guide being shaped to deform the flexible sheet between the laterally unfurled condition and the deployed tubular condition.

4. The deployable tube apparatus of claim 3, wherein the guide comprises:
a splitter that separates the coupled first and the second lateral margins; and
a fastener having an orifice through which the first and the second lateral margins pass, the orifice being sized to cooperate with the first and the second lateral margins to compress the first and the second lateral margins together.

5. The deployable tube apparatus of claim 1, further comprising a spooling mechanism configured to wind the flexible sheet about the spool.

6. The deployable tube apparatus of claim 5, wherein the spooling mechanism comprises a biasing element applying a continuous biasing force to spool the flexible sheet in the laterally unfurled condition.

7. The deployable tube apparatus of claim 1, wherein the first lateral margin comprises a first fastener portion and the second lateral margin comprises a second fastener portion attachable to the first fastener portion to maintain the flexible sheet in the deployed tubular condition.

8. The deployable tube apparatus of claim 7, wherein the first fastener portion comprises a longitudinally extending groove and the second fastener portion comprises a longitudinally extending protrusion receivable in the groove.

9. The deployable tube apparatus of claim 7, wherein:
a) the first fastener portion is disposed on an edge of the first lateral margin and the second fastener portion is disposed on an edge of the second lateral margin, the first and the second fastener portions being attachable to place the first and the second lateral margins in an edge to edge configuration, or
b) the first fastener portion is disposed on a face of the first lateral margin and the second fastener portion is disposed on a face of the second lateral margin, the first and the second fastener portions being attachable to place the first and the second lateral margins in a face-to-face configuration.

10. A deployable tube apparatus, comprising:
a flexible sheet material having longitudinal length, a first lateral margin, and a second lateral margin, the first and the second lateral margins extending along the longitudinal length, the sheet material being bendable between a laterally unfurled condition where the first and the second lateral margins are spaced from each other and a deployed tubular condition where the first and the second lateral margins are adjacent to each other to form a lumen, at least one of the first and second lateral margins comprising a fastener portion that selectively attaches the first and the second lateral margins; and
a guide configured to fold the flexible sheet material from the laterally unfurled condition to the deployed tubular condition and to fasten the first and the second lateral margins.

11. The deployable tube apparatus of claim 10, wherein the guide comprises:
a splitter that separates the attached first and the second lateral margins; and
an opening sized to receive the first and the second lateral margins and compress the first and the second lateral margins toward each other.

12. The deployable tube apparatus of claim 10, comprising:
a spool disposed spatially to the guide, the spool configured to coil the flexible sheet material from the deployed tubular condition to the laterally unfurled condition.

13. The deployable tube apparatus of claim 10, wherein the guide comprises:
a splitter that separates the attached first and second lateral margins; and
a slide fastener having an orifice through which the first and the second lateral margins pass, the orifice being sized to cooperate with the first and the second lateral margins to compress the first and the second lateral margins together.

14. The deployable tube apparatus of claim 10, further comprising a spooling mechanism comprising a biasing element applying a continuous biasing force to spool the sheet material in the laterally unfurled condition.

15. The deployable tube apparatus of claim 10, wherein the fastener portion is a first fastener portion on the first lateral margin and the second lateral margin comprises a second fastener portion attachable to the first fastener portion to maintain the sheet material in the deployed tubular condition.

16. A deployable tube apparatus for guiding an elongated flexible surgical instrument, the apparatus comprising:
a flexible sheet material having a longitudinal length, a first lateral margin, and a second lateral margin, the first and the second lateral margins extending along the longitudinal length, the sheet material being deployable from a laterally unfurled condition with the first and the second lateral margins spaced from each other to a deployed tubular condition where the first and the second lateral margins are adjacent to each other to form a lumen arranged to provide lateral support to the elongated flexible surgical instrument, at least one of the first and second lateral margins comprising a fastener that selectively attaches the first and the second lateral margins; and
a guide structurally arranged to selectively fasten and unfasten the fastener of said at least one of the first and the second lateral margins when the sheet material displaces past the guide, the guide being shaped to deform the sheet material between the laterally unfurled condition and the deployed tubular condition.

17. The deployable tube apparatus of claim 16, wherein the guide comprises a fixture through which the elongated flexible surgical instrument extends, the fixture being disposed to align the elongated flexible surgical instrument with the lumen formed by the flexible sheet material when in the deployed tubular condition so that an inner wall of the flexible sheet material in the deployed tubular condition provides lateral support to the elongated surgical instrument.

18. The deployable tube apparatus of claim 16, further comprising:
   a spool about which the sheet material is wound when in the laterally unfurled condition, and
   a biasing element biasing the spool to a rolled configuration with the sheet material toward the laterally unfurled condition.

19. The deployable tube apparatus of claim 16, wherein the guide is shaped to form an opening sized to receive the first and the second lateral margins and compress the first and the second lateral margins toward each other; and
   wherein the guide includes a boss disposed in the opening positioned to separate the first and second lateral margins.

20. The deployable tube apparatus of claim 1, wherein the proximal attachment element includes a passage extending therethrough.

* * * * *